United States Patent [19]

Brandes et al.

[11] Patent Number: 4,990,528

[45] Date of Patent: Feb. 5, 1991

[54] MIXTURE OF FUNGICIDAL AGENTS

[75] Inventors: Wilhelm Brandes, Leichlingen; Helmut Kaspers, Leverkusen; Paul Reinecke, Leverkusen; Hans Scheinpflug, Leverkusen; Wolfgang Krämer, Wuppertal, all of Fed. Rep. of Germany

[73] Assignee: Bayer Aktiengesellschaft, Leverkusen, Fed. Rep. of Germany

[21] Appl. No.: 398,113

[22] Filed: Aug. 24, 1989

Related U.S. Application Data

[60] Division of Ser. No. 22,454, Mar. 6, 1987, Pat. No. 4,888,349, which is a continuation of Ser. No. 649,463, Sep. 11, 1984, abandoned, which is a division of Ser. No. 468,729, Feb. 22, 1983, Pat. No. 4,514,402.

[30] Foreign Application Priority Data

Mar. 6, 1982 [DE] Fed. Rep. of Germany ....... 3208142

[51] Int. Cl.$^5$ ...................... A01N 43/64; A01N 47/28
[52] U.S. Cl. ...................................... 514/383; 514/596
[58] Field of Search ................................ 514/383, 596

[56] References Cited

U.S. PATENT DOCUMENTS

| | | | |
|---|---|---|---|
| 3,658,813 | 4/1972 | Godefroi et al. | 548/336 |
| 3,952,002 | 4/1976 | Kramer et al. | 548/255 |
| 4,038,406 | 7/1977 | Meiser et al. | 514/383 |
| 4,048,318 | 9/1977 | Meiser et al. | 514/383 |
| 4,053,616 | 10/1977 | Poüchel et al. | 514/383 |
| 4,060,623 | 11/1977 | Meiser et al. | 514/383 |
| 4,127,673 | 11/1978 | Yamada et al. | 514/585 |
| 4,147,791 | 4/1979 | Meiser et al. | 514/383 |
| 4,156,001 | 5/1979 | Brandes et al. | 514/245 |
| 4,251,512 | 2/1981 | Brandes et al. | 424/162 |

FOREIGN PATENT DOCUMENTS

| | | | |
|---|---|---|---|
| 0040007 | 11/1981 | European Pat. Off. | 514/383 |
| 7300301 | 7/1973 | Netherlands | 514/383 |

Primary Examiner—Allen J. Robinson
Attorney, Agent, or Firm—Sprung Horn Kramer & Woods

[57] ABSTRACT

A synergistic fungicidal composition comprising

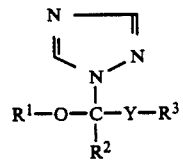

in which
$R^1$ represents optionally substituted phenyl,
$R^2$ represents hydrogen, alkyl having up to 4 carbon atoms or phenyl,
$R^3$ represents alkyl having up to 6 carbon atoms, cycloalkyl having 5 to 6 carbon atoms, phenyl or 4-chlorophenyl, and
Y represents the CO group, the group

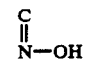

of $C(OH)_2$
or $CH(OH)$,
and at least one of several specifically identified additional fungicides.

2 Claims, No Drawings

MIXTURE OF FUNGICIDAL AGENTS

This is a division of application Ser. No. 022,454, filed Mar. 6, 1987, now U.S. Pat. No. 4,888,349, which is a continuation of application Ser. No. 649,463, filed Sept. 11, 1984, now abandoned, which is a divisional of application Ser. No. 468,729, filed Feb. 22, 1986, now U.S. Pat. No. 4,514,402.

The present invention relates to new fungicidal active compound combinations comprising known 1,2,4-triazole derivatives of phenoxyether-ketones and phenoxyether-alkanols and other known fungicidal active compounds.

It has already been disclosed that 1,2,4-triazole derivatives of phenoxyether-ketones and phenoxyetheralkanols, such as, for example, 1-(4-chlorophenoxy)-3,3-dimethyl-1-(1,2,4-triazol-1-yl)-butan-2-one and the corresponding butan-2-ol derivative, have a good action against fungi which damage plants (in this context, see the German Patent Specifications No. 2,201,064 and U.S. Pat. No. 3,952,002), and in particular the action against powdery mildew fungi should be mentioned, as well as against rust diseases, leaf spot diseases and smut diseases in various crop plants.

The following fungicidal active compounds or active compound groups have likewise been disclosed:

(A) Quinoxaline derivatives, such as, for example, 6-methyl-quinoxaline-2,3-cycl.-dithiolcarbonate (CHINO-METHIONAT) and quinoxaline-2,3-cycl.-trithiocarbonate (CHINOTHIONAT) (in this context, see the data in R. Wegler, "Chemie der Pflanzenschutz- und Schädlingsbekämpfungsmittel" (Chemistry of plant protection agents and pestcombating agents), volume 2, pages 128 and 129, Springer-Verlag, Berlin/Heidelberg/New York, 1970);

(B) Derivatives of imidazoles and triazoles, such as, for example, allyl 1-(2,4-dichlorophenyl)-2-imidazol-1-yl-ethyl ether (FUNGAFLOR), 2-(imidazol-1-ylmethyl)-2-phenyl-hexanenitrile (FENAPRONIL), 1-cyclohexyl-2-(1,2,4-triazol-1-yl)-3-hydroxy-4,4-dimethyl-pent-1-ene, 1-[2-(2,4-dichlorophenyl)-4-propyl-1,3-dioxolan-2-ylmethyl]-1H-1,2,4-triazole (PROPICONAZOL), 1-[2-(2,4-dichlorophenyl)-4-ethyl-1,3-dioxolan-2-yl]-methyl-1H-1,2,4-triazole (ETACONAZOLE), 1-(2,4-dichlorophenyl)-2-(1,2,4-triazol-1-yl)-4,4-dimethyl-pentan-3-ol (DICLOBUTRAZOL), 1-(4-chlorophenyl)-2-(1,2,4-triazol-1-yl)-4,4-dimethylpentan-3-ol, 1-(2,4-dichlorophenyl)-2-(1,2,4-triazol-1-yl)-3-hydroxy-4,4-dimethyl-pent-1-ene, 1-(4-chlorophenyl)-2-(1,2,4-triazol-1-yl)-3-hydroxy-4,4-dimethyl-pent-1-ene and 4-(n-butyl)-4H-1,2,4-triazole (TRIAZBUTIL) (in this context, see DE-OS (German Published Specification No.) 2,429,523, DE-OS (German Published Specification No.) 2,063,857, DE-OS (German Published Specification No.) 2,604,047, U.S. Application Ser. No. 294,603 filed Aug. 20, 1981, now pending, DE-OS (German Published Specification No.) 2,551,560, DE-OS (German Published Specification No.) 2,737,489, DE-OS (German Published Specification No.) 3,010,560 and U.S. Patent Specification No. 3,647,810).

(C) Derivatives of phenylureas, such as, for example, 1-phenyl-3-cyclopentyl-3-(4-chlorobenzyl)-urea (PENCYCURON), see German Patent Specification No. 2,732,257;

(D) Bis-trifluoromethylimino five-membered ring compounds, such as, for example, 2-phenylimino-3-phenyl-4,5-bis-(trifluoromethylimino)-thiazolidine (FLUBENZIMINE), and the compound of the formula

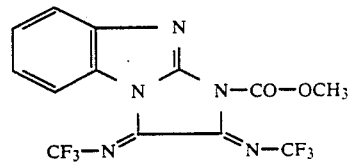

(in this connection, see U.S. Pat. No. 3,895,020 and U.S. Pat. No. 3,787,435.

(E) Derivatives of 3-azolyl-benzo-1,2,4-triazines and -benzo-1,2,4-triazine-1-oxides, such as, for example, 3-imidazolyl-7-chloro-benzo-1,2,4-triazine-1-oxide (see U.S. Pat. No. 4,239,760);

(F) Copper salts of organic compounds, such as, for example, the copper salt of 8-hydroxyquinoline (see R. Wegler, loc. cit., page 112);

(G) Specific alkylated derivatives of methyl benzimidazole-2-carbamate, such as, for example, the methyl ester of 4-methyl- and of 5-methyl-benzimidazole-2-carbamic acid (see U.S. Patent Specification No. 2,933,502 and U.S. Patent Specification No. 2,933,504 and DE-OS (German Published Specification No. 2,217,919 (Le A 14 420)).

The activity of the abovementioned individual active compounds is not always completely satisfactory in particular fields of use.

It has now been found that new active compound combinations comprising 1,2,4-triazole derivatives of phenoxyether-ketones and phenoxyether-alkanols of the formula

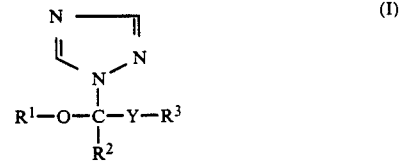

in which
R$^1$ represents phenyl which can be optionally substituted by halogen, nitro, trifluoromethyl, alkyl having up to 6 carbon atoms, alkoxy having up to 4 carbon atoms, phenyl and 4-chlorophenyl,
R$^2$ represents hydrogen, alkyl having up to 4 carbon atoms or phenyl,
R$^3$ represents alkyl having up to 6 carbon atoms, cycloalkyl having 5 to 6 carbon atoms, phenyl or 4-chlorophenyl, and
Y represents the CO group, the group

or C(OH)$_2$ or CH(OH), and
(A) quinoxaline derivatives of the formula

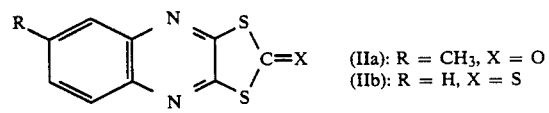

and/or (B) derivatives of imidazoles and triazoles of the formulae

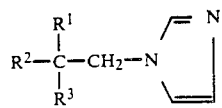

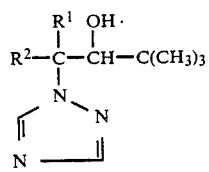

(IIIa): $R^1$ = H, $R^2$ = CH$_2$=CH—CH$_2$—O $R^3$ = 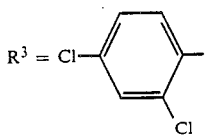

(IIIb): $R^1$ = CN, $R^2$ =

$R^3$ = C$_4$H$_9$ (IIIc): $R^1$ and $R^2$ together =

(IIId): $R^1$ and $R^2$ together =

(IIIe): $R^1$ and $R^2$ together =

(IIIf): $R^1$ = H, $R^2$ =

(IIIg): $R^1$ = H, $R^2$ =

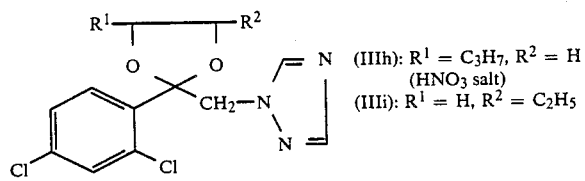

(IIIh): $R^1$ = C$_3$H$_7$, $R^2$ = H (HNO$_3$ salt)
(IIIi): $R^1$ = H, $R^2$ = C$_2$H$_5$

(IIIk)

and/or
(C) a phenylurea of the formula

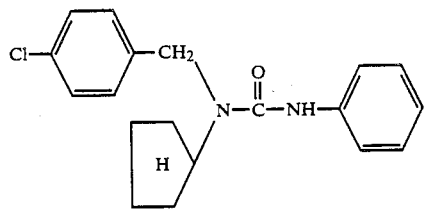

(IV)

and/or (D) bis-trifluoromethylimino five-membered ring compounds of the formulae

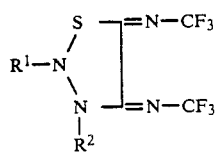

(Va): $R^1$ = $R^2$ = 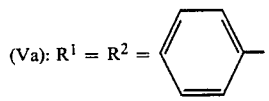

and

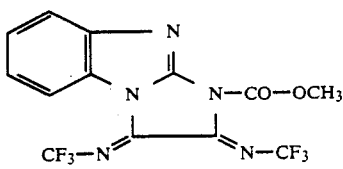
(Vb)

and/or (E) a 3-azolyl-benzo-1,2,4-triazine derivative of the formula

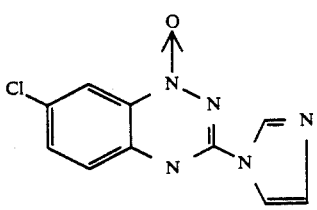
(VI)

and/or (F) a copper complex salt of the formula

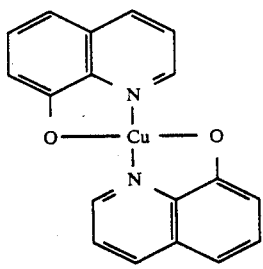
(VII)

and/or (G) a derivative, alkylated in the nucleus, of methyl benzimidazole-2-carbamate of the formula

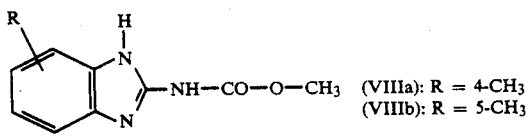

(VIIIa): R = 4-CH₃
(VIIIb): R = 5-CH₃ or comprising mixtures of (VIIIa) and (VIIIb) have a particularly high fungicidal activity.

Surprisingly, the fungicidal action of the active compound combinations according to the invention is substantially higher than the action of the individual components and may also be substantially higher than the sum of the individual components (synergistic effect). The addition of active compounds from the abovementioned groups (A), (B), (C), (D), (E), (F) and (G) to the 1,2,4-triazole derivatives of the formula I represents an enrichment of the art.

The general formula I gives the definition of the 1,2,4-triazole derivatives of phenoxyether-ketones and phenoxyether-alkanols to be used for the combination according to the invention. In this formula, $R^1$ represents phenyl which can be optionally preferably monosubstituted to trisubstituted by fluorine, chlorine, nitro, trifluoromethyl, methyl, methoxy and phenyl. $R^2$ preferably represents hydrogen, $R^3$ preferably represents straight-chain or branched alkyl having 1 to 4 carbon atoms, phenyl and 4-chlorophenyl, and Y has the preferred meanings CO or CH(OH). The following compounds of the formula I with the substituent meanings given in each case may be mentioned as typical examples of particularly preferred 1,2,4-triazole derivatives of phenoxyether-ketones and phenoxyether-alkanols:

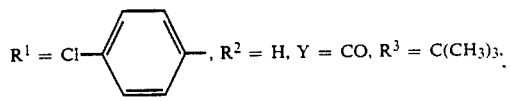
Ia

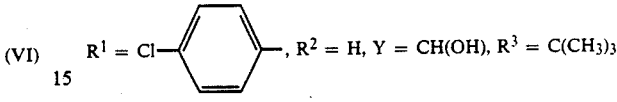
Ib

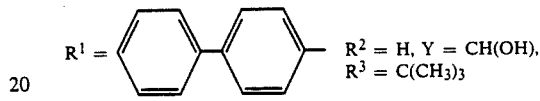
Ic

All three compounds listed, which have the common names TRIADIMEFON (Ia), TRIADIMENOL (Ib) and BITERTANOL (Ic) are generally known (in this connection, see the U.S. Pat. Nos. 3,912,752 and 3,952,002.

Formulae IIa and IIb represent the quinoxaline derivatives (group A) optionally to be used as components of the mixture. The compounds having the common names CHINOMETHIONAT (IIa) and CHINOTHIONAT (IIb) are generally known (see the prior art data above). Preferred mixtures are those which contain in the first place one of the 1,2,4-triazole derivatives of phenoxyether-ketones and phenoxyether-alkanols mentioned as examples (see the data above concerning the compounds of the formula I) and CHINOMETHIONAT (formula IIa) as the second component.

Formulae IIIa to IIIk represent the derivatives of imidazoles and triazoles (group B) which may furthermore be used as components of the mixture. The compounds are known (see the prior art data). Preferred mixtures are those which contain in the first place one of the 1,2,4-triazole derivatives of the phenoxyether-ketones and phenoxyether-alkanols mentioned as examples and in the second place an active compound of the formula IIIa (FUNGAFLOR) or IIIc (1-cyclohexyl-2-(1,2,4-triazol-1-yl)-3-hydroxy-4,4-dimethyl-pent-1-ene.

Formula IV represents the phenylurea (group C) which may furthermore be used as a component of the mixture. The compound having the common name PENCYCURON is known (see the prior art data). Preferred mixtures are those which contain in the first place one of the 1,2,4-triazole derivatives of phenoxyether-ketones and phenoxyether-alkanols mentioned as examples and in the second place the active compound of the formula IV.

Formulae Va to Vc represent the bis-trifluoromethylimino five-membered ring compounds (group D) which may furthermore be used as components of the mixture. The compounds are known (see the prior art data). Preferred mixtures are those which contain in the first place one of the 1,2,4-triazole derivatives of phenoxyether-ketones and phenoxyether-alkanols mounted as examples, and FLUBENZIMINE (formula Va) as the second component.

Formula VI represents the 3-azolyl-benzo-1,2,4-triazine derivative (group E) which may furthermore be used as a component of the mixture. The compound is known (see the prior art data). Preferred mixtures are those which contain in the first place one of the 1,2,4-triazole derivatives of phenoxyether-ketones and phenoxyetheralkanols mentioned as examples and in the second place the active compound of the formula VI.

Formula VII represents the copper complex salt (group F) which may furthermore be used as a component of the mixture. The compound is known (see the prior art data. Preferred mixtures are those which contain in the first place one of the 1,2,4-triazole derivatives of phenoxyether-ketones and phenoxyether-alkanols mentioned as examples and in the second place the active compound of the formula VII.

Formulae VIIIa and VIIIb represent the derivatives of methyl benzimidazole-2-carbamate which are alkylated in the nucleus (group G) and which may furthermore be used as components of the mixture. The compounds are known (see the prior art data). Preferred mixtures are those which contain in the first place one of the 1,2,4-triazole derivatives of phenoxyether-ketones and phenoxyether alkanols mentioned as examples, and the active compounds of the formulae VIIIa and VIIIb as the second component; in this case, the second component can also be present as a mixture of VIIIa and VIIIb.

In addition to the mixture components of the groups (A), (B), (C), (D), (E), (F) and (G), which, in accordance with the present invention, are to be used as a mixture with the 1,2,4-triazole derivatives of phenoxyether-ketones and phenoxyether-alkanols of the formula (I), it is also possible to use the following components for the mixture: Pyrimidine derivatives, such as 2-dimethylamino-4-hydroxy-5-butyl-6-methyl-pyrimidine (DIMETHIRIMOL) and 2-ethylamino-4-hydroxy-5-butyl-6-methyl-pyrimidine (ETHIRIMOL); Dimethylamidosulphonates, such as 2-ethylamino-5-n-butyl-6-methyl-pyrimidin-4-yl-dimethylsulphonate (BUPIRIMATE); Morpholine derivatives, such as 4-tridecyl-2,6-dimethylmorpholine (TRIDEMORPH) and 4-[3-(4-tert.-butyl-phenyl)-2-methyl-propyl]-2,6-dimethyl-morpholine (FENPROPEMORPH); Piperazine derivatives, such as N,N'-bis-(1-formamido-2,2,2-trichloroethyl)-piperazine (TRIFORINE); Phenylpyrimidine derivatives, such as α-(2-chlorophenyl)-α-(4-chlorophenyl)-α-(pyrimidin-5-yl)-methanol (FENARIMOL) and α-(2-chlorophenyl)-α-(4-fluorophenyl)-α-(pyrimidin-5-yl)-methanol (NUARIMOL); Carboxylic acid anilides, such as 2-iodobenzoic acid anilide (BENODAMIL), 2-methyl-5,6-dihydro-4-H-pyran-3-carboxylic acid anilide (PYRACARBOLID), 2,4,5-trimethyl-3-furanecarboxylic acid anilide (METHFUROXAM) and 2-methyl-N-[3-(1-methylethoxy)-phenyl]-benzamide (Bi 2459).

Dicarboximides, such as 1,2-dimethyl-cyclopropanedicarboxylic acid N-(3,5-dichlorophenyl)-imide (PROCYMIDONE), 3-(3,5-dichlorophenyl)-5-methyl-5-vinyl-1,3-oxazolidine-2,4-dione (VINCHLOZOLIN), 3-(3,5-dichlorophenyl)-2,4-dioxo-1-(N-isopropyl)-imidazolidine-carboxamide (IPRODIONE), ethyl 3-(3,5-dichlorophenyl)-5-methyl-2,4-dioxo-oxazolidine-5-carboxylate (CARBOZOLINE) and N-(p-fluorophenyl)-2,3-dichloromaleinimide FLUOROIMID); Acylalanines, such as methyl N-(2,6-dimethylphenyl)-N-(2-methoxy-acetyl)-alanine (METAXANINE), methyl N-(2-furoyl)-N-(2,6-xyly)-alamine (FURALAXYL), 2-chloro-N-(2,6-dimethylphenyl)-N-(tetrahydro-2-oxo-3-furanyl)-acetamide (MILFURAM), methyl N-(2,6-dimethylphenyl)-N-(phenylacetyl)-alanine (BENALAXYL) AND 2,6-dimethyl-N-(1-methoximino-prop-2-yl)-N-methoxyacetylaniline; Alkoxy-imino-cyano-acetamides, such as N-ethylaminocarbonyl-2-cyano-2-methoximino-acetamide (CYMOXANIL); Alkyl phosphites, such as the aluminum salt of O-ethyl phosphite (ALUMINIUMPHOSAETHYL); Guanidinamines, such as bis-(8-guanidinooctyl)-amine sulphate (GUAZATINE); Cyclopropanecarboxylic acid amides, such as N-(3-chlorophenyl)-N-(tetrahydro-2-oxo-3-furanyl)-cyclopropanecarboxylic acid amide (CYPROFURAM).

The abovementioned active compounds may also be added as a further component (for example as a third component) to a mixture of a 1,2,4-triazole derivative of phenoxyether-ketones and phenoxyether-alkanols and an active compound from the groups (A) to (G).

The weight ratios of the active compound groups in the active compound combinations can vary within relatively wide ranges. In general, 0.02 to 500 parts by weight of active compound from the active compound classes (A) to (G), preferably 0.2 to 200 parts by weight of the latter, particularly preferably 1 to 50 parts by weight, are employed per part by weight of 1,2,4-triazole derivative of the formula I.

The active compound combinations according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compound combinations according to the invention have a very broad action spectrum and can be used against parasitic fungi which infest above-ground parts of plants or which attack the plants from the ground, as well as pathogens which can be transferred by seeds. Such active compound combinations are of particular practical importance as seed-dressing agents against phytopathogenic fungi which are transferred with the seed or occur in the ground and infest the crop plants from there. These are seedling diseases, root rots, and stalk, stem, leaf, flower, fruit and seed diseases which are caused in particular by Tilletia, Urocystis, Ustilago, Septoria, Typhula, Rhynchosporium, Helminthosporium and Fusarium species. Owing to the systemic action of one component of the mixture, the plants are also protected, frequently even for a relatively long time after dressing, from pathogens which can attack the various parts of the shoot, for example powdery mildew fungi and rust fungi. In addition, the active compound combinations can also be employed as soil-treatment agents against phytopathogenic fungi, and are active against root rots and tracheomycoses which are caused, for example, by pathogens of the genera Pythium, Verticillium, Philaophora, Rhizoctonia, Fusarium and Thielaviopsis.

However, the active compound combinations according to the invention, when applied directly to the above-ground parts of plants, also exhibit an outstanding action against pathogens on various crop plants, such as powdery mildew fungi (Erysiphe, Uncinula, Sphaerotheca and Podosphaera species, and Leveillula taurica), rust fungi, Venturia species, Cercospora species, Alternaria species, Botrytis species, Phytophthora species, Peronospora species, Pyricularia oryzae and Pellicularia sasakii.

The active compound combinations can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellent, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules and latices, such as gum arabic, polyvinyl alcohol and polyvinyl acetate can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and tin.

The formulations in general contain between 0.1 and 95% weight of active compound, preferably between 0.5 and 90%.

The active compound combinations according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The use examples which follow serve for illustration. The active compounds which, for example, are to be used in active compound combinations according to the invention are listed in the following list:

| Active compound No. | Formula | Common name | Literature |
|---|---|---|---|
| 1 | Ia | TRIADIMEFON | German Patent Specification 2,201,063<br>U.S. Patent Specification 3,912,752 |
| 2 | Ib | TRIADIMENOL | German Patent Specification 2,324,010<br>U.S. Patent Specification 3,952,002 |
| 3 | Ic | BITERTANOL | as in the case of compound 2 |
| 4 | IIa | CHINOMETHIONAT | R. Wegler (loc. cit.) vol. 2, page 128 |
| 5 | IIb | CHINOTHIONAT | R. Wegler (loc. cit.) vol. 2, page 129 |

-continued

| Active compound No. | Formula | Common name | Literature |
|---|---|---|---|
| 6 | IIIa | FUNGAFLOR | DE-OS (German Published Specification) 2,063,857 U.S. Patent Specification 3,658,813 |
| 7 | IIIb | FENAPRONIL | DE-OS (German Published Specification) 2,604,047 French Patent Specification 2,300,081 |
| 8 | IIIc | | DE-OS (German Published Specification) 2,906,061 U.S. Specification S.N. 294,603 filed 8/20/81, now pending |
| 9 | IIId | | DE-OS (German Published Specification) 3,010,560 British Patent Specification 2,046,260 |
| 10 | IIIe | | as for compound 9 |
| 11 | IIIf | DICLOBUTRAZOL | DE-OS (German Published Specification) 2,737,489 French Patent Specification 2,362,133 |
| 12 | IIIg | | as in the case of compound 11 |
| 13 | IIIh | PROPICONAZOL (proposed) | German Patent Specification 2,551,560 British Patent Specification 1,522,657 |
| 14 | IIIi | ETACONAZOLE (proposed) | as in the case of compound 13 |
| 15 | IIIk | TRIAZBUTIL | R. Wegler (loc. cit.), vol. 4, page 210 U.S. Patent Specification 3,647,810 |
| 16 | IV | PENCYCURON | German Patent Specification 2,732,257 U.S. Patent Specification 4,127,673 |
| 17 | Va | FLUBENZIMINE | German Patent Specification 2,062,348 U.S. Patent Specification 3,895,020 |
| 18 | Vb | | DE-OS (German Published Specification) 2,062,346 U.S. Patent Specification 3,787,435 U.S. Patent Specification 3,934,019 |
| 19 | VI | | DE-OS (German Published Specification) 2,802,488 U.S. Patent Specification 4,239,760 |
| 20 | VII | OXINE-COPPER | R. Wegler, loc. cit., page 112 |
| 21 | VIIIa | | U.S. Patent Specification 2,933,502 U.S. Patent Specification 2,933,504 |
| 22 | VIIIb | | DE-OS (German Published Specification) 2,217,919 U.S. Patent Specification 3,993,846 |

EXAMPLE A

Erysiphe test (barley) / protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

TABLE A

| | Erysiphe test (barley)/protective | |
|---|---|---|
| Active compound | Active compound concentration in the spray liquor in % by weight | Disease infestation in % of the untreated control |
| 1 (TRIADIMEFON) (known) | 0.00025 | 25.0 |
| | 0.0001 | 66.3 |
| 4 (CHINOMETHIONAT) (known) | 0.00025 | 100 |
| | 0.0001 | 100 |
| Mixture of 1 and 4 (Mixing ratio 1:1) | 0.00025 +0.00025 | 12.5 |
| Mixture of 1 and 4 (Mixing ratio 1:1) | 0.0001 +0.0001 | 25.0 |

EXAMPLE B

Sphaerotheca test (cucumber) / protective

To test for protective activity, young plants are sprayed with a commercial formulation until dripping wet. After the spray coating has dried on, the plants are dusted with conidia of the fungus Sphaerotheca fuliginea.

The plants are then placed in a greenhouse at 23 to 24° C. and at a relative atmospheric humidity of about 75%.

Evaluation is carried out 10 days after the inoculation.

TABLE B

| | Sphaerotheca test (cucumber)/protective | |
|---|---|---|
| Active compound | Active compound concentration | Infestation in % |
| 1 (TRIADIMEFON) (known) | 0.00006% | 50 |
| 4 (CHINOMETHIONAT) (known) | 0.00006% | 96 |
| Mixture of 1 and 4 (Mixing ratio 1:1) | 0.00006% +0.00006% | 38 |

EXAMPLE C

Drechslera graminea test (barley) / seed treatment (syn. Helminthosporium gramineum)

The active compounds are used as dry dressings. These are produced by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

TABLE C

| | Drechslera graminea test (barley)/seed treatment (syn. Helminthosporium gramineum) | |
|---|---|---|
| Active compound | Amount of active compound applied in mg/kg of seed | Diseased plants in % of the total plants which have emerged |
| not dressed | — | 28.8 |
| 2 (TRIADIMENOL) (known) | 200 | 12.3 |
| 19 (Compound of the formula (VI)) (known) | 10 | 4.9 |
| 6 (FUNGAFLOR) (known) | 10 | 8.3 |
| Mixture of 2 and 19 (Mixing ratio 1:0.05) | 200 +10 | 0.0 |
| Mixture of 2 and 6 (Mixing ratio 1:0.05 | 200 +10 | 0.0 |

EXAMPLE D

Leptosphaeria nodorum test (wheat) / protective
Solvent: 100 parts by weight of dimethylformamide
Emulsifier: 0.25 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Leptosphaeris nodorum. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is carried out 10 days after the inoculation.

TABLE D

| | Leptosphaeria nodorum test (wheat)/protective | |
|---|---|---|
| Active compound | Active compound concentration in the spray liquor in % weight | Disease infestation in % of the untreated control |
| 1 TRIADIMEFON) (known) | 0.01 | 100 |
| 17 (FLUBENZIMINE) (known) | 0.01 | 50 |
| 21 (Compound of the formula VIIIa) (known) | 0.0025 | 82.5 |
| Mixture of 1 and 17 (Mixing ratio 1:1) | 0.01 +0.01 | 25.0 |
| Mixture of 1 and 21 (Mixing ratio 1:0.25) | 0.01 +0.0025 | 50.0 |

EXAMPLE E

Pyrenophora teres test (barley) / protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Pyrenophora teres. The plants remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

TABLE E

Pyrenophora teres test (barley)/protective

| Active compound | Active compound concentration in the spray liquor in % by weight | Disease infestation in % of the untreated control |
|---|---|---|
| 1 (TRIADIMEFON) (known) | 0.005 | 100 |
| 8 (Compound of the formula (IIIc)) (known) | 0.01 | 100 |
| Mixture of 1 and 8 (Mixing ratio 1:2) | 0.005 +0.01 | 21.3 |

It will be appreciated that the instant specification and examples are set forth by way of illustration and not limitation, and that various modifications and changes may be made without departing from the spirit and scope of the present invention.

What is claimed is:

1. A fungicidal composition comprising a synergistic fungicidally effective amount of a mixture of
a 1,2,4-triazole derivative of a phenoxyetheralkanol of the formula

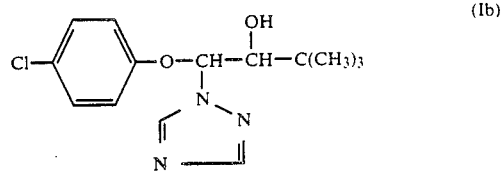

and
a phenylurea of the formula

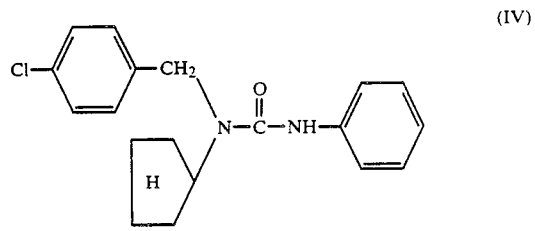

wherein the synergistic weight ratio of (Ib) to (IV) is from about 1:1 to 1:50.

2. A process for combating fungi which comprises applying to fungi or their habitat a synergistic fungicidally effective amount of a composition according to claim 1.

* * * * *